United States Patent
Klein et al.

(10) Patent No.: US 9,750,784 B2
(45) Date of Patent: Sep. 5, 2017

(54) INTRAARTICULAR APPLICATION OF PEPSTATIN IN THE CASE OF ARTHROSIS

(71) Applicant: Merck Patent GmbH, Darmstadt (DE)

(72) Inventors: Markus Klein, Darmstadt (DE); Ralf Wodopia, Weinheim (DE); Hans Guehring, Eltville (DE); Sven Lindemann, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/910,317

(22) PCT Filed: Jul. 7, 2014

(86) PCT No.: PCT/EP2014/001861
§ 371 (c)(1),
(2) Date: Feb. 5, 2016

(87) PCT Pub. No.: WO2015/018472
PCT Pub. Date: Feb. 12, 2015

(65) Prior Publication Data
US 2016/0175381 A1 Jun. 23, 2016

(30) Foreign Application Priority Data
Aug. 6, 2013 (EP) .................................. 13003923

(51) Int. Cl.
*A61K 38/08* (2006.01)
*A61K 9/00* (2006.01)

(52) U.S. Cl.
CPC ............ *A61K 38/08* (2013.01); *A61K 9/0019* (2013.01)

(58) Field of Classification Search
CPC ................................. A61K 38/08; C07K 7/02
See application file for complete search history.

(56) References Cited

U.S. PATENT DOCUMENTS

| 3,906,085 A | 9/1975 | Miller | |
| 2005/0042213 A1* | 2/2005 | Gelder | A61K 31/075 424/94.64 |
| 2013/0316955 A1 | 11/2013 | Klein et al. | |
| 2015/0225369 A1* | 8/2015 | Wucherer-Plietker | C07D 213/75 514/235.5 |

FOREIGN PATENT DOCUMENTS

| JP | 2000-300266 A | 10/2000 |
| WO | 2012/107153 A1 | 8/2012 |

OTHER PUBLICATIONS

International Search Report dated Sep. 22, 2014 issued in corresponding PCT/EP2014/001861 application (pp. 1-3).
English Abstract of JP 2000-300266 A published Oct. 31, 2000.
(Continued)

*Primary Examiner* — Jeffrey E Russel
(74) *Attorney, Agent, or Firm* — Millen, White, Zelano, Branigan, P.C.

(57) ABSTRACT

The present invention relates to pharmaceutical preparations and medicaments for intraarticular administration, comprising pepstatin, and to the preparation and use thereof, in particular in the treatment and/or prophylaxis of arthrosis, traumatic cartilage injuries, arthritis, pain, allodynia or hyperalgesia, particularly preferably in arthrosis.

12 Claims, 5 Drawing Sheets

(56) References Cited

OTHER PUBLICATIONS

R. Ruechel et al., "Modulation of Experimental Systematic Murine Candidosis by Intravenous Pepstatin", Database Biosis [Online] Biosciences Information Service, XP-002137713 (1990).
M.F. Powell et al., "Peptide Stability in Drug Development: A Comparison of Peptide Reactivity in Different Biological Media", Journal of Pharmaceutical Sciences, vol. 81, No. 8 (Aug. 1992) pp. 731-735.
M.F. Powell et al., "Peptide Stability in Drug Development. II. Effect of Single Amino Acid Substitution and Glycosylation on Peptide Reactivity in Human Serum", Pharmaceutical Research, vol. 10, No. 9 (1993) pp. 1268-1273.
M. Werle et al., "Strategies to Improve Plasma Half Life Time of Peptide and Protein Drugs", Amino Acids, vol. 30 (2006) pp. 351-367.

\* cited by examiner

Fig. 1: Stability data of pepstatin in synovial fluid:
| Time (h) | % remaining | +/- remaining |
|---|---|---|
| 0 | 100 | 0.000 |
| 6 | 100 | 0.002 |
| 24 | 98.4 | 0.016 |
| 48 | 92.0 | 0.083 |
| 72 | 90.3 | 0.102 |
| 144 | 91.3 | 0.0912 |
| 216 | 89.9 | 0.106 |
| 312 | 71.6 | 0.335 |
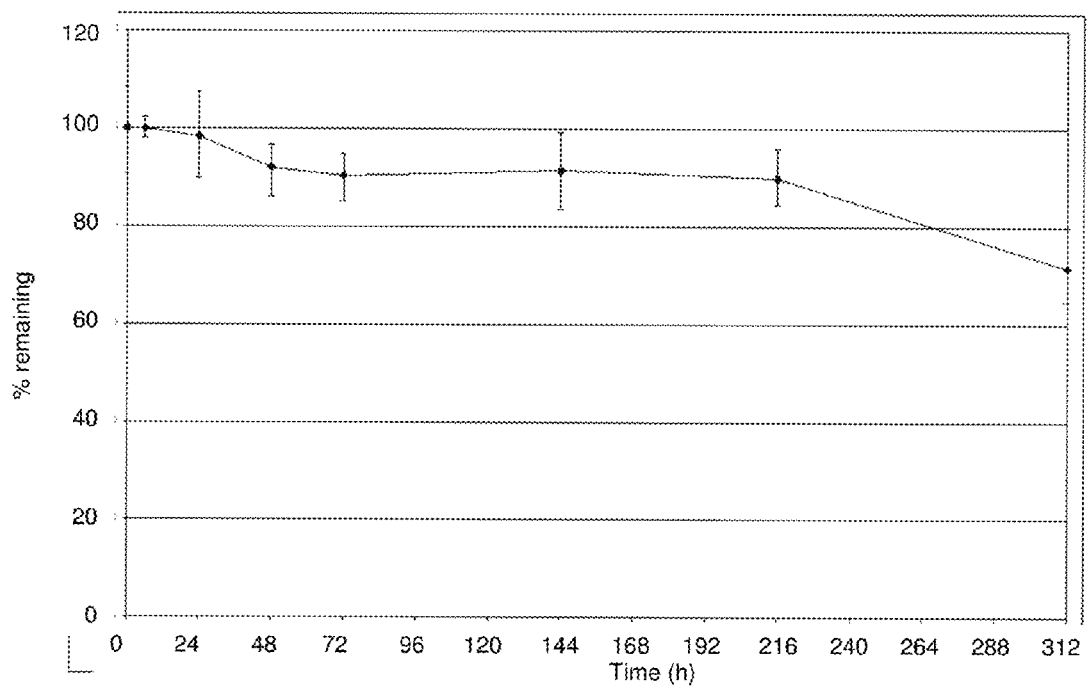

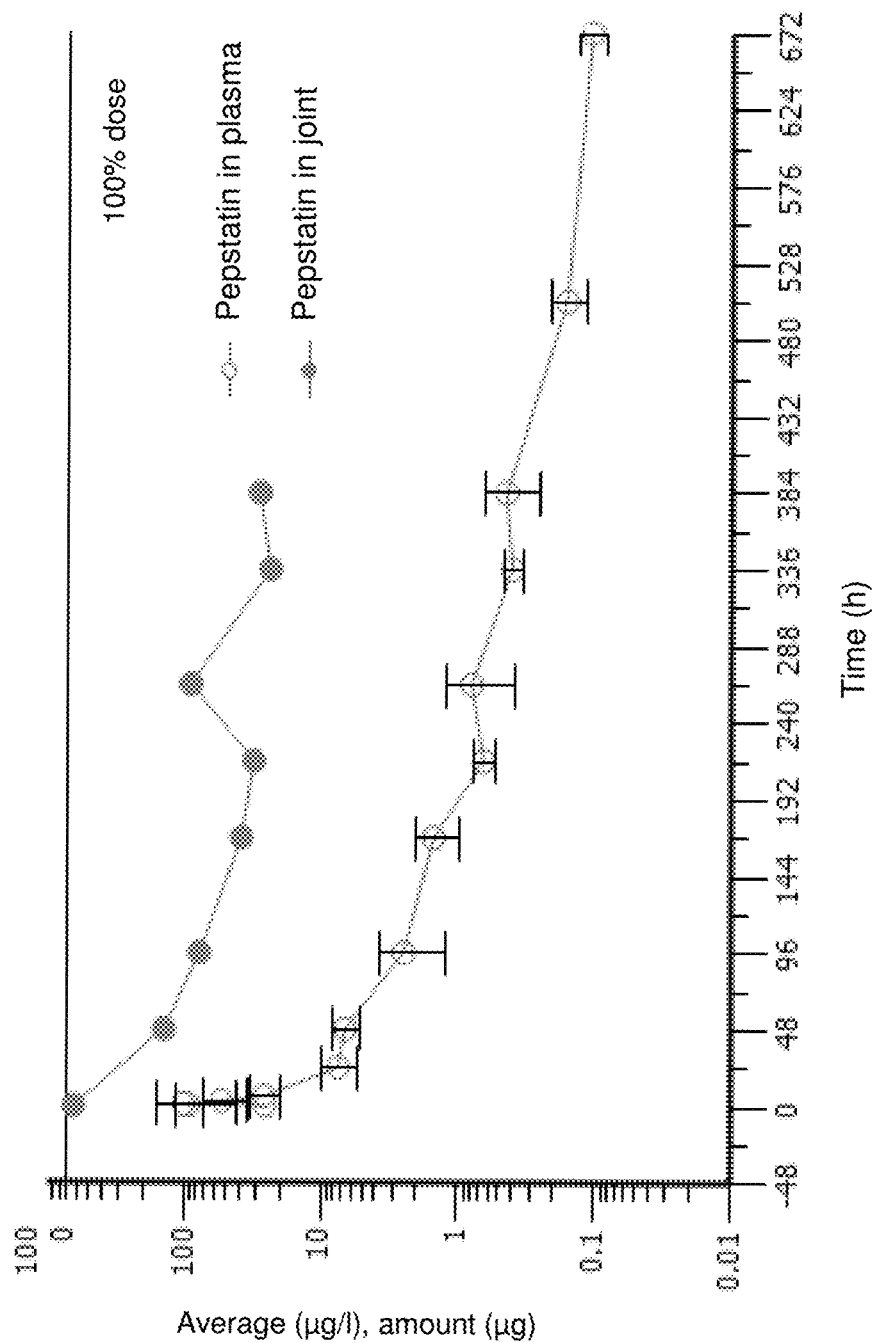
Fig. 2: Pharmacokinetics – residence time of pepstatin in the joint and in the plasma after intraartiular administration Fig. 3: Pharmacokinetics – residence time of pepstatin in the plasma after intravenous and oral administration Dose-standardised plasma concentrations (C [ng/ml] / dose [mg/ml] and pharmacokinetic parameters of pepstatin after intravenous (iv) and oral (po) administration in male rats.

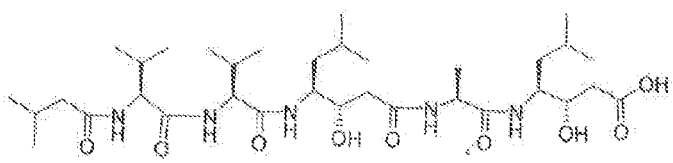

| | | |
|---|---|---|
| Molecular structure | | |
| Admin. | iv | po |
| Dose [mg/kg] | 0.2 | 0.5 |
| Matrix | plasma | plasma |
| time [h] | | |
| 0.1 | 395 | ND |
| 0.25 | ND | <LLOQ |
| 0.5 | 17.7 | <LLOQ |
| 1 | 4.19 | <LLOQ |
| 2 | <LLOQ | <LLOQ |
| 4 | <LLOQ | <LLOQ |
| 6 | <LLOQ | <LLOQ |
| 24 | <LLOQ | <LLOQ |
| Parameter | | |
| $C_{max}$ [ng/ml] / dose [mg/kg] | 395 | <LLOQ |
| $t_{max}$ [h] | 0.100 | NA |
| AUC [h · ng/ml] / dose [mg/kg] | | |
| 0 – t last | 113 | NA |
| 0 – ∞ | 114 | |
| $t_{½}$ [h] | | |
| 0.1 – t last | 0.140 | |
| CL [L/h/kg] | 6.76 | |
| Vss [L/kg] | 1.31 | |

Recovery [% of dose] of unchanged active compound in faeces and urine (0–24 h collection)

| | | |
|---|---|---|
| Faeces | 52 | 37 |
| Urine | 1.8 | <1 |
| Bioavailability (%) | | <5 |
| $CL_{int}$ [µl/min/mg] | <10 | |
| Fub [%] | >29 | |
| Free $C_{max}$ @ 1mg/kg [nM] | >173 | NA |
| Biochemical $IC_{50}$ [nM] | <1 | |
| Cellular $IC_{50}$ [nM] | NA | |

Fig 4: ACTL model
| Pepstatin | PVP Lutrol | Control (cl) |
|---|---|---|
| 4 | 21 | 5 |
| 8 | 12 | 4 |
| 15 | 17 | 9 |
| 13 | 22 | 5 |
| 24 | 21 | 6 |
| 9 | 20 | 2 |
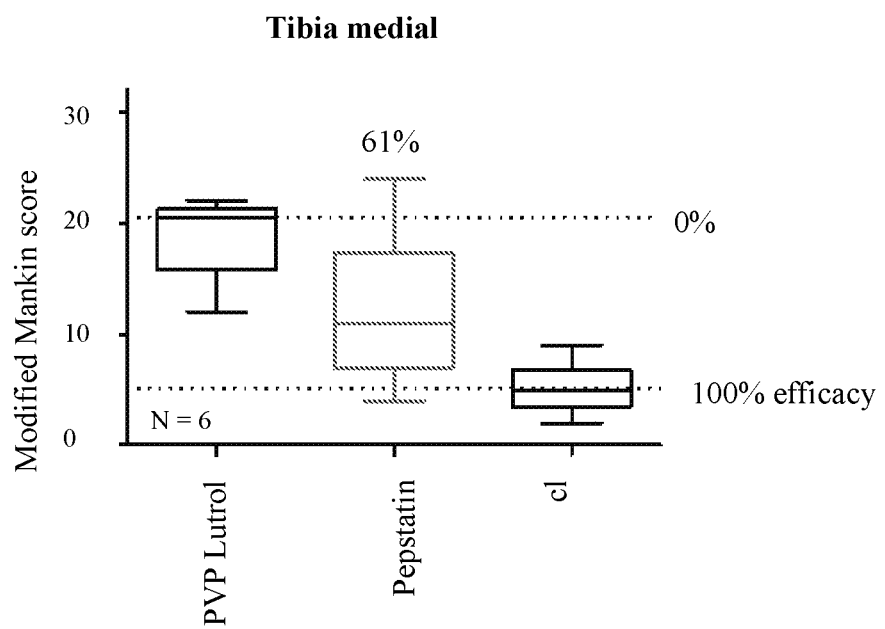

INTRAARTICULAR APPLICATION OF PEPSTATIN IN THE CASE OF ARTHROSIS

The present invention relates to pharmaceutical preparations and medicaments for intraarticular administration, comprising pepstatin, and to the preparation thereof and in particular to the use thereof in the treatment and/or prophylaxis of arthrosis, traumatic cartilage injuries, arthritis, pain, allodynia or hyperalgesia, particularly preferably in arthrosis.

BACKGROUND OF THE INVENTION

Arthrosis is the most widespread joint disease worldwide, and radiological signs of arthrosis are found in the majority of over-65 year olds. In spite of this major importance for the health system, the causes of arthrosis remain unclear to date, and effective preventative measures furthermore remain a distant aim. A reduction in the joint gap (caused by destruction of the joint cartilage), together with changes in the subchondral bone and osteophyte formation, are the radiological characteristics of the disease. For the patient, however, pain (load-dependent and nocturnal rest pain) with subsequent function impairments are to the fore. It is also these which force the patient into social isolation with corresponding secondary diseases.

The term arthrosis according to an unofficial definition in Germany denotes "joint wear" which exceeds the usual extent for the age. The causes are regarded as being excessive stress (for example increased body weight), connatal or traumatic causes, such as malpositioning of the joints or also bone deformations due to bone diseases, such as osteoporosis. Arthrosis can likewise arise as a consequence of another disease, for example joint inflammation (arthritis) (secondary arthrosis), or accompany overload-induced effusion (secondary inflammation reaction) (activated arthrosis). The Anglo-American specialist literature differentiates between osteoarthritis [OA], in which the destruction of the joint surfaces can probably be attributed principally to the effects of load, and rheumatoid arthritis [RA], in which joint degeneration due to an inflammatory component is to the fore.

In principle, arthrosis is also differentiated according to its cause. Arthrosis alcaptonurica is based on increased deposition of homogenitic acid in joints in the case of previously existing alkaptonuria. In the case of haemophilic arthrosis, regular intraarticular bleeding occurs in the case of haemophilia (haemophilic joint). Arthrosis urica is caused by the mechanical influence of urate crystals (uric acid) on the healthy cartilage (W. Pschyrembel et al.: Klinisches Wörterbuch mit klinischen Syndromen und einem Anhang Nomina Anatomica [Clinical Dictionary with Clinical Syndromes and a Nomina Anatomica Annex]. Verlag Walter de Gruyter & Co, 253rd Edition, 1977).

The classical cause of arthrosis is dysplasia of joints. Using the example of the hip, it becomes clear that the zone with the greatest mechanical stress in the case of a physiological hip position represents a significantly larger area than in the case of a dysplastic hip. However, the stresses caused by the forces acting on the joint are substantially independent of the joint shape. They are essentially distributed over the main stress zone(s). A greater pressure will thus arise in the case of a relatively small zone than in the case of a larger one. The biomechanical pressure on the joint cartilage is thus greater in the case of a dysplastic hip than in the case of a physiological hip position. This rule is generally regarded as the cause of the increased occurrence of arthrotic changes in weight-bearing joints which differ from the ideal anatomical shape.

If the consequences of an injury are responsible for premature wear, the term post-traumatic arthrosis is used. Further causes of secondary arthrosis that are being discussed are mechanical, inflammatory, metabolic, chemical (quinolones), trophic, hormonal, neurological and genetic reasons. In most cases, however, the diagnosis given is idiopathic arthrosis, by which the doctor means an apparent absence of a causal disease (H. I. Roach and S. Tilley, Bone and Osteoarthritis F. Bronner and M. C. Farach-Carson (Editors), Verlag Springer, Volume 4, 2007).

Medicinal causes of arthrosis can be, for example, antibiotics of the gyrase inhibitor type (fluoroquinolones, such as ciprofloxacin, levofloxacin). These medicaments result in complexing of magnesium ions in poorly vascularised tissues (hyaline joint cartilage, tendon tissue), which has the consequence that irreversible damage occurs to connective tissue. This damage is generally more pronounced in the growth phase in children and juveniles. Tendinopathies and arthropathies are known side effects of this class of medicaments. In adults, these antibiotics result in accelerated physiological degradation of the hyaline joint cartilage according to information from independent pharmacologists and rheumatologists (M. Menschik et al., Antimicrob. Agents Chemother. 41, 1997, pp. 2562-2565; M. Egerbacher et al., Arch. Toxicol. 73, 2000, pp. 557-563; H. Chang et al., Scand. J. Infect. Dis. 28, 1996, pp. 641-643; A. Chaslerie et al., Therapie 47, 1992, p. 80). Extended treatment with phenprocoumone can also encourage arthrosis by decreasing bone density in the case of stresses of the joint internal structure.

Besides age, known risk factors for osteoarthrosis are mechanical overload, (micro)traumas, joint destabilisation caused by loss of the securing mechanisms, and genetic factors. However, neither the occurrence nor possible interventions have been fully explained (H. I. Roach and S. Tilley, Bone and Osteoarthritis F. Bronner and M. C. Farach-Carson (Editors), Verlag Springer, Volume 4, 2007).

In a joint affected by arthrosis, the content of nitrogen monoxide is increased at times. A similar situation has been observed due to strong mechanical irritation of cartilage tissue (P. Das et al., Journal of Orthopaedic Research 15, 1997, pp. 87-93. A. J. Farrell et al. Annals of the Rheumatic Diseases 51, 1992, pp. 1219-1222; B. Fermor et al., Journal of Orthopaedic Research 19, 2001, pp. 729-737), whereas moderate mechanical stimulation tends to have a positive effect. The action of mechanical forces is thus causally involved in the progress of osteoarthrosis (X. Liu et al., Biorheology 43, 2006, pp. 183-190).

In principle, arthrosis therapy pursues two aims. Firstly freedom from pain under normal load and secondly the prevention of mechanical restrictions or changes in a joint. These aims cannot be achieved in the long term by pain treatment as a purely symptomatic therapy approach, since this cannot halt the progress of the disease. If the latter is to be achieved, the cartilage destruction must be stopped. Since the joint cartilage in adult patients cannot regenerate, the elimination of pathogenetic factors, such as joint dysplasia or malpositioning, which result in increased point pressure on the joint cartilage, is in addition enormously important.

Finally, it is attempted to prevent or stop the degeneration processes in the cartilage tissue with the aid of medicaments.

An essential factor for the functioning state of the joint cartilage and thus the resistance thereof to stress is the extracellular matrix, which primarily consists of collagens, proteoglycans and water. The enzymes involved in degradation of the extracellular matrix include, in particular, the metalloproteases, aggrecanases and the cathepsin enzymes. However, further enzymes can in principle also degrade cartilage matrix, for example plasmin, kallikrein, neutrophil elastase, tryptase and chymase.

Cathepsins belong to the papain superfamily of lysosomal proteases. Cathepsins are involved in normal proteolysis and the conversion of target proteins and tissues, and in the initiation of proteolytic cascades and proenzyme activations. In addition, they are involved in MHC class II expression (Baldwin (1993) Proc. Natl. Acad. Sci., 90: 6796-6800; Mixuochi (1994) Immunol. Lett., 43: 189-193). However, abnormal cathepsin expression can result in severe diseases. Thus, increased cathepsin expression has been detected in cancer cells, for example in breast, lung, prostate, glioblastoma and head and neck cancer, and it has been shown that cathepsins are associated with inadequate therapy success in breast, lung, head and neck cancer, and in brain tumours (Kos et al. (1998) Oncol. Rep., 5: 1349-1361; Yan et al. (1998) Biol. Chem., 379: 113-123; Mort et al.; (1997) Int. J. Biochem. Cell Biol., 29: 715-720; Friedrick et al. (1999) Eur. J Cancer, 35: 138-144). In addition, abnormal cathepsin expression is apparently involved in the development of inflammatory and non-inflammatory diseases, such as, for example, rheumatoid arthritis and osteoarthrosis (Keyszer (1995) Arthritis Rheum., 38: 976-984).

The molecular mechanism of cathepsin activity has not been fully explained. On the one hand, it has been found that, for example, induced cathepsin expression protects B cells from which serum is taken against apoptosis, and that treatment of the cells with antisense oligonucleotides of cathepsin B induces apoptosis (Shibata et al. (1998) Biochem. Biophys. Res. Commun., 251: 199-20; Isahara et at. (1999) Neuroscience, 91: 233-249). These reports suggest an anti-apoptotic role of cathepsins. However, they are in complete contrast to earlier reports, which describe cathepsins as apoptosis mediators (Roberts et al (1997) Gastroenterology, 113: 1714-1726; Jones et al. (1998) Am. J. Physiol., 275: G723-730).

Cathepsins are synthesised as inactive zymogens on ribosomes and transferred into the lysosomal system. After proteolytic cleaving-off of the N-terminal propeptide, the cathepsin concentration in the acidic environment of the lysosomes increases to 1 mM, and the cathepsins are released into the extracellular medium by the lysosomes.

In the case of cathepsins, a differentiation is made between the cysteine cathepsins B, C, H, F, K, L, O, S, V and W, the aspartyl cathepsins D and E and the serine cathepsin G.

Examples of cathepsin inhibitors in clinical development are cathepsin K inhibitors for the treatment of arthrosis and cathepsin S inhibitors for the treatment of arthritis, neuropathic pain and psoriasis.

Besides cathepsin D, the aspartyl proteases also include the HIV aspartyl protease (HIV-1 protease), renin, pepsin A and C, BACE (Asp2, memapsin), plasmepsins and the aspartyl haemoglobinases (Takahashi, T. et al., Ed. Aspartic Proteinases Structure, Function, Biology and Biomedical Implications (Plenum Press, New York, 1995), Adams, J. et al., Ann. Rep. Med. Chem. 31, 279-288, 1996; Edmunds J. et al., Ann. Rep. Med. Chem. 31, 51-60, 1996; Miller, D. K. et al., Ann. Rep. Med. Chem 31, 249-268, 1996). Cathepsin D is normally involved in the degradation of intracellular or phagocytised proteins and thus plays an important role in protein metabolism (Helseth, et al., Proc. Natl. Acad. Sci. USA 81, 3302-3306, 1984), in protein catabolism (Kay, et al., Intracellular Protein Catabolism (eds. Katunuma, et al., 155-162, 1989) and in antigen processing (Guagliardi, et al., Nature, 343, 133-139, 1990; Van Noort, et al., J. Biol. Chem., 264, 14159-14164, 1989).

Increased cathepsin D levels are associated with a number of diseases. Thus, increased cathepsin D levels correlate with a poor prognosis in breast cancer and with increased cell invasion and an increased risk of metastases, and shorter relapse-free survival time after therapy and a lower survival rate overall (Westley B. R. et al., Eur. J. Cancer 32, 15-24, 1996; Rochefort, H., Semin. Cancer Biol. 1:153, 1990; Tandon, A. K. et al., N. Engl. J. Med. 322, 297, 1990). The cathepsin D secretion rate in breast cancer is promoted by overexpression of the gene and by modified processing of the protein. Increased levels of cathepsin D and other proteases, such as, for example, collagenase, produced in the immediate vicinity of a growing tumour, could degrade the extracellular matrix in the area surrounding the tumour and thus promote the detachment of tumour cells and invasion into new tissue via the lymph and circulation system (Liotta L. A., Scientific American February:54, 1992; Liotta L. A. and Stetler-Stevenson W. G., Cancer Biol. 1:99, 1990; Liaudet E., Cell Growth Differ. 6:1045-1052, 1995; Ross J. S., Am. J. Clin. Pathol. 104:36-41, 1995; Dickinson A. J., J. Urol. 154:237-241, 1995).

Cathepsin D is in addition associated with degenerative changes in the brain, such as, for example, Alzheimer's disease. Thus, cathepsin D is associated with cleavage of the amyloid-β precursor protein or of a mutant precursor which increases the expression of the amyloid protein in transfected cells (Cataldo, A. M. et al., Proc. Natl. Acad. Sci. 87: 3861, 1990; Ladror, U. S. et al., J. Biol. Chem. 269: 18422, 1994, Evin G., Biochemistry 34: 14185-14192, 1995). The amyloid-β protein, which is formed by proteolysis of the amyloid-β precursor protein, results in the formation of plaques in the brain and appears to be responsible for the development of Alzheimer's disease. Increased cathepsin D levels have also been found in the cerebrospinal fluid of Alzheimer's patients, and a high proteolytic activity of cathepsin D compared with the mutant amyloid-β precursor protein has been found (Schwager, A. L., et al. J. Neurochem. 64:443, 1995). In addition, a significant increase in cathepsin D activity is measured in biopsies from Huntington's disease patients (Mantle D., J. Neurol. Sci. 131: 65-70, 1995).

Cathepsin D is thought to play an essential role at various levels in the development of arthrosis. Thus, increased mRNA levels of cathepsin D are measured in the joint cartilage of the hip joint head in dogs with spontaneous arthrosis compared healthy dogs (Clements D. N. et al., Arthritis Res. Ther. 2006; 8(6): R158; Ritchlin C. et al., Scand. J. Immunnol. 40: 292-298, 1994). Devauchelle V. et al. (Genes Immun. 2004, 5(8): 597-608) also show different expression rates of cathepsin D in human patients in the case of arthrosis compared with rheumatoid arthritis (see also Keyszer G. M., Arthritis Rheum. 38: 976-984, 1995). Cathepsin D also appears to play a role in mucolipidosis (Kopitz J., Biochem. J. 295, 2: 577-580, 1993).

The lysosomal endopeptidase cathepsin D is the most widespread proteinase in the chondrocytes (Ruiz-Romero C. et al., Proteomics. 2005, 5(12): 3048-59). In addition, the proteolytic activity of cathepsin D has been detected in the cultivated synovium from osteoarthrosis patients (Bo G. P. et al., Clin. Rheumatol. 2009, 28(2): 191-9), and increased proteolytic activity is also found in synovectomy tissue of patients with rheumatoid arthritis (Taubert H. et al., Autoimmunity. 2002, 35(3): 221-4). Lorenz et al. (Proteomics. 2003, 3(6): 991-1002) thus also write that, although the lysosomal and secreted aspartyl protease cathepsin D has not yet been studied in detail with respect to arthritis and arthrosis, in contrast to cathepsins B and L, Lorenz et al. found, however, higher protein levels of cathepsin D in the synovial tissue of patients with arthrosis compared with patients with rheumatoid arthritis.

Gedikoglu et al. (Ann. Rheum. Dis. 1986, 45(4): 289-92) have likewise detected increased proteolytic activity of cathepsin D in synovial tissue and Byliss and Ali (Biochem. J. 1978, 171(1): 149-54) in the cartilage of patients with arthrosis.

In the case of arthrosis, a local reduction in the pH occurs in regions of the cartilage. This reduction in the pH is of crucial importance for the understanding of catabolic processes in the cartilage.

In the case of arthrosis, a direct correlation is thus also found between a low pH in the joint tissue and the severity and progress of the disease. At a pH of 5.5, autodigestion of the cartilage occurs. This can be inhibited virtually completely by pepstatin or ritonavir in explant cultures (for example from mouse, cow or human). This suggests an essential role, or even a key role, of cathepsin D in arthrosis, since pepstatin inhibits aspartyl proteases with one exception—BACE1—and only these two aspartyl proteases have hitherto been identified in the cartilage tissue. Thus, Bo G. P. et al. (Clin. Rheumatol. 2009, 28(2): 191-9) also describe the important role of cathepsin D in pathological changes in joints.

The best-known aspartyl protease inhibitor is pepstatin, a peptide which was originally isolated from a *Streptomyces* culture. Pepstatin is effective against pepsin, cathepsin and renin. Many aspartyl protease inhibitors have therefore been modelled on the example of the structure of pepstatin (U.S. Pat. No. 4,746,648; Umezawa, H., et al., J. Antibiot (Tokyo) 23: 259-62, 1970; Morishima, H., et al., J. Antibiot. (Tokyo) 23: 263-5, 1970; Lin, T. and Williams, H. R., J. Biol. Chem. 254: 11875-83, 1979; Jupp, R. A., et al., Biochem. J. 265: 871-8, 1990; Agarwal, N. S. and Rich, D. H., J. Med. Chem. 29: 2519-24, 1986; Baldwin, E. T., et al., Proc. Natl. Acad. Sci., USA 90: 6796-800, 1993; Francis, S. E. et al., EMBO J 13: 306-17, 1994).

Aspartyl proteases and cathepsin D are frequently described as target proteins for active compounds for the treatment of neurodegenerative diseases, cognitive disorders, dementia, Alzheimer's, cancer, malaria, HIV infection and diseases of the cardiovascular system, and inhibitors of aspartyl proteases or cathepsin D are disclosed for the treatment of these diseases, such as, for example, in WO 2009013293, EP 1987834, EP 1872780, EP 1867329, EP 1745778, EP 1745777, EP 1745776, WO 1999002153, WO 1999055687, U.S. Pat. No. 6,150,416, WO 2003106405, WO 2005087751, WO 2005087215, WO 2005016876, US 2006281729, WO 2008119772, WO 2006074950, WO 2007077004, WO 2005049585, U.S. Pat. No. 6,251,928 and U.S. Pat. No. 6,150,416.

Although the known cathepsin D inhibitors and the two model compounds pepstatin and ritonavir effectively inhibit cathepsin D activity, they have, however, quite low selectivity for other aspartyl proteases. The role of the renin-angiotensin system (RAS) in the regulation of blood pressure and the fluid and electrolyte balance (Oparil, S. et al., N. Engl. J. Med. 1974; 291: 381-401/446-57) and the efficacy of renin and pepsin inhibitors in diseases of the cardiovascular system is adequately known, and thus numerous side effects can be expected, in particular on oral or systemic administration of these low-selectivity cathepsin D inhibitors, and systemic complications can also be expected on local application due to the diffusion to be expected of the compounds into the blood.

In addition, peptidic compounds in particular generally have low stability in plasma, synovial fluid and fluids of other compartments and they undergo very rapid metabolic degradation, meaning that a short residence time in the blood, in the joint capsule and other compartments can be expected.

Thus, Powell, M. F. et al. (J. Pharm. Sciences, Vol. 81, No. 8, 731-735, 1992) investigated the stability of peptidic compounds in pooled human serum and in pooled synovial fluid of patients having rheumatic arthritis (see p. 731, right-hand column, penultimate paragraph). In Tables 1 and 2, Powell et al. disclosed that most of the modified and unmodified peptides tested having a length of 10 to 25 amino acids have a half life of less than one hour in the media tested, human plasma (HS), synovial fluid (SF), foetal calf serum (FCS) or mouse liver homogenate (MLH) (see page 735, right-hand column, final paragraph). The stability of the peptidic compounds in pooled human serum and pooled synovial fluid of patients having arthritis is basically similarly low (see page 733).

Against the background of the low stability and short residence time of peptidic compounds in plasma and owing to the side effects to be expected that are described above, oral or systemic administration of peptidic cathepsin D inhibitors does not come into consideration for the treatment of arthrosis.

Intraarticular administration of peptidic compounds is generally also considered unsuitable by the person skilled in the art owing to the short half life to be expected in synovial fluid, but in particular owing to the short residence time to be expected in the joint capsule (diffusion via the synovial membrane and degradation) and owing to the systemic side effects to be expected due to diffusion into the plasma.

In particular, the short half life of peptidic compounds of a few hours according to Powell et al. (1992) means that frequent intraarticular injections would be necessary. However, injections into the joint gap are associated with pain and a significant risk of infection for the patient and such injections should therefore not be carried out more frequently than at an interval of two to four weeks.

The object of the present invention was therefore to find novel medicaments and pharmaceutical preparations which can be employed for the prevention and treatment of arthrosis and are sufficiently stable in synovial fluid in the case of local or intraarticular administration and only diffuse through the synovial membrane into the plasma to a slight extent and thus have a long residence time in the joint capsule, so that the active-compound concentration remains in the therapeutically effective range over the longest possible period after injection.

SUMMARY OF THE INVENTION

Surprisingly, it has been found that pepstatin, in spite of high clearance in the case of intravenous or oral administration, remains in the joint capsule or in the synovial fluid in a concentration significantly above the $IC_{50}$ and thus in the pharmacologically effective concentration over a longer period in the case of intraarticular injection of a suspension. In addition, pepstatin, in spite of its peptidic structure, exhibits surprisingly high stability in synovial fluid (see example) and thus pepstatin significantly exceeds even the longest stabilities measured by Powell et al. of peptidic compounds in synovial fluid (see Powell et al. Table II on page 733: No. 8 pertussis toxin having a half life of barely two days in synovial fluid, No. 15 *Myobacterium leprae* having a half life of about seven and a half hours, all other peptidic compounds having half lives of a few minutes), and only this surprisingly high stability and the surprisingly long residence time in the joint capsule enable medically relevant use of pepstatin in the treatment of arthrosis, since pepstatin does not, as was to be expected according to Powell et al., remain in the joint capsule at clinically relevant levels for only a few hours, but instead is present in a concentration significantly above the $IC_{50}$ for more than two weeks.

Pepstatin is thus, surprisingly, suitable for medicaments and pharmaceutical preparations which are administered locally or intraarticularly for the prevention and treatment of arthrosis and remain at high levels over a long period, so that the medicaments and pharmaceutical preparations according to the invention only have to be administered intraarticularly at most weekly, preferably at intervals of one to several months.

Pepstatin is a highly effective inhibitor of cathepsin D, and few side effects are to be expected in the case of intraarticular administration for the treatment of arthrosis, since pepstatin, owing to its long residence time in the joint capsule and slow release from the synovium, only achieves low systemic levels (plasma levels) in the case of intraarticular administration.

In particular, the long residence time of pepstatin in the joint capsule is surprising and therapeutically valuable, since, on the basis of the investigations by, for example, Powell et al. (1992), low stability of peptidic compounds in synovial fluid would have been expected and in addition high release of peptidic compounds of small size from the synovium into the plasma would have been expected, both processes which would result in a short residence time in the joint capsule. Surprisingly, however, pepstatin, contrary to expectations, has a long residence time in the joint capsule, since both its stability in synovial fluid is high, and also the release from the synovium is apparently very low.

The invention therefore relates to a pharmaceutical preparation for intraarticular administration, comprising pepstatin ((3S,4S)-3-hydroxy-4-[(S)-2-((3S,4S)-3-hydroxy-6-methyl-4-{(S)-3-methyl-2-[(S)-3-methyl-2-(3-methyl-butyrylamino)butyrylamino]butyrylamino}heptanoylamino)propionylamino]-6-methylheptanoic acid) and/or one of its physiologically acceptable salts, derivatives, solvates, prodrugs and stereoisomers, including mixtures thereof in all ratios.

The invention also relates to a pharmaceutical preparation according to the invention of this type, comprising further excipients and/or adjuvants.

In addition, the invention relates to an above pharmaceutical preparation according to the invention, comprising at least one further medicament active compound.

The invention also relates to pharmaceutical preparations for intraarticular administration, comprising peptidic cathepsin D inhibitors which have similar properties to pepstatin, namely cathepsin D inhibition in the nanomolar range, high stability in synovial fluid and a long residence time in the joint capsule.

Pepstatin contains a number of centres of chirality, so that the invention also relates to the use of the optically active forms (stereoisomers), the enantiomers, racemates, diastereomers and hydrates and solvates of pepstatin.

Pharmaceutically or physiologically acceptable derivatives are taken to mean, for example, salts of pepstatin, and also so-called prodrug compounds. Prodrug compounds are taken to mean pepstatin derivatives which have been modified by means of, for example, alkyl or acyl groups (see also amino- and hydroxyl-protecting groups below), sugars or oligopeptides and which are rapidly cleaved or liberated in the organism to form the effective pepstatin molecules. These also include biodegradable polymer derivatives of pepstatin, as described, for example, in Int. J. Pharm. 115 (1995), 61-67. Pepstatin can be used in its final non-salt form. On the other hand, the present invention also encompasses the use of pepstatin in the form of its pharmaceutically acceptable salts, which can be derived from various organic and inorganic bases by procedures known in the art. Pharmaceutically acceptable salt forms of pepstatin are for the most part prepared by conventional methods. Since pepstatin contains a carboxyl group, one of its suitable salts can be formed by reacting pepstatin with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of pepstatin are likewise included.

Furthermore, the base salts of pepstatin include aluminium, ammonium, calcium, copper, iron(III), iron(II), lithium, magnesium, manganese(III), manganese(II), potassium, sodium and zinc salts, but this is not intended to represent a restriction.

Of the above-mentioned salts, preference is given to ammonium; the alkali metal salts sodium and potassium, and the alkaline-earth metal salts calcium and magnesium. Salts of pepstatin which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

As mentioned, the pharmaceutically acceptable base-addition salts of pepstatin are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of pepstatin are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

In view of that stated above, it can be seen that the term "pharmaceutically acceptable salt" in the present connection is taken to mean an active compound which comprises pepstatin in the form of one of its salts, in particular if this salt form imparts improved pharmacokinetic properties on the active compound compared with the free form of the active compound or any other salt form of the active compound used earlier. The pharmaceutically acceptable salt form of the active compound can also provide this active compound for the first time with a desired pharmacokinetic property which it did not have earlier and can even have a positive influence on the pharmacodynamics of this active compound with respect to its therapeutic efficacy in the body.

Solvates of pepstatin are taken to mean adductions of inert solvent molecules pepstatin which form owing to their mutual attractive force. Solvates are, for example, hydrates, such as monohydrates or dihydrates, or alcoholates, i.e. addition compounds with alcohols, such as, for example, with methanol or ethanol.

It has been found that pepstatin is well tolerated and has valuable pharmacological properties, since it selectively inhibits aspartyl proteases and in particular cathepsin D.

The invention therefore furthermore relates to the use of pepstatin for the preparation of a medicament for intraarticular administration for the treatment and/or prophylaxis of diseases which are caused, promoted and/or propagated by cathepsin D and/or by cathepsin D-promoted signal transduction.

The invention thus also relates, in particular, to a medicament for intraarticular administration comprising pepstatin and/or one of its physiologically acceptable salts, derivatives, solvates, prodrugs and stereoisomers, including mixtures thereof in all ratios, for use in the treatment and/or prophylaxis of physiological and/or pathophysiological conditions.

Particular preference is given, in particular, to physiological and/or pathophysiological conditions which are connected to cathepsin D.

Physiological and/or pathophysiological conditions are taken to mean medically relevant physiological and/or pathophysiological conditions, such as, for example, diseases or illnesses and medical disorders, complaints, symptoms or complications and the like, in particular diseases.

The invention furthermore relates to a medicament for intraarticular administration comprising pepstatin and/or one of its physiologically acceptable salts, derivatives, solvates, prodrugs and stereoisomers, including mixtures thereof in all ratios, for use in the treatment and/or prophylaxis of physiological and/or pathophysiological conditions, selected from the group consisting arthrosis, traumatic cartilage injuries and arthritis, in particular rheumatoid arthritis. Particular preference is given to the use in the treatment and/or prophylaxis of arthrosis.

Pain is a complex sensory perception which, as an acute event, has the character of a warning and control signal, but as chronic pain has lost this and in this case (as chronic pain syndrome) should nowadays be regarded and treated as an independent syndrome. Hyperalgesia is the term used in medicine for excessive sensitivity to pain and reaction to a stimulus which is usually painful. Stimuli which can trigger pain are, for example, pressure, heat, cold or inflammation. Hyperalgesia is a form of hyperaesthesia, the generic term for excessive sensitivity to a stimulus. Allodynia is the term used in medicine for the sensation of pain which is triggered by stimuli which do not usually cause pain.

The invention furthermore relates to a medicament for intraarticular administration comprising pepstatin and/or one of its physiologically acceptable salts, derivatives, solvates, prodrugs and stereoisomers, including mixtures thereof in all ratios, for use in the treatment and/or prophylaxis of physiological and/or pathophysiological conditions, selected from the group consisting of pain, allodynia and hyperalgesia.

The invention thus particularly preferably relates to a medicament for intraarticular administration comprising pepstatin and/or one of its physiologically acceptable salts, derivatives, solvates, prodrugs and stereoisomers, including mixtures thereof in all ratios, for use in the treatment and/or prophylaxis of physiological and/or pathophysiological conditions, selected from the group consisting of arthrosis, traumatic cartilage injuries, arthritis, pain, allodynia and hyperalgesia, particularly preferably for use in the treatment and/or prophylaxis of arthrosis.

It is intended that the medicaments disclosed above include a corresponding use of pepstatin for the preparation of a medicament for intraarticular administration for the treatment and/or prophylaxis of the above physiological and/or pathophysiological conditions.

It is additionally intended that the medicaments disclosed above include a corresponding method for intraarticular administration for the treatment and/or prophylaxis of the above physiological and/or pathophysiological conditions in which pepstatin is administered intraarticularly to a patient in need of such a treatment.

The invention thus preferably relates to the use of a pharmaceutical preparation according to the invention for intraarticular administration in the treatment and/or prophylaxis of physiological and/or pathophysiological conditions, selected from the group consisting of arthrosis, traumatic cartilage injuries, arthritis, pain, allodynia or hyperalgesia.

The invention particularly preferably relates here to the use of a pharmaceutical preparation according to the invention for intraarticular administration in the treatment and/or prophylaxis of arthrosis.

The invention thus also preferably relates to the use of pepstatin and/or one of its physiologically acceptable salts, derivatives, solvates, prodrugs and stereoisomers, including mixtures thereof in all ratios, for intraarticular administration in the treatment and/or prophylaxis of physiological and/or pathophysiological conditions, selected from the group consisting of arthrosis, traumatic cartilage injuries, arthritis, pain, allodynia and hyperalgesia.

The invention particularly preferably relates here to the use of pepstatin and/or one of its physiologically acceptable salts, derivatives, solvates, prodrugs and stereoisomers, including mixtures thereof in all ratios, for intraarticular administration in the treatment and/or prophylaxis of arthrosis.

The invention also relates to the use of peptidic cathepsin D inhibitors which have similar properties to pepstatin, namely cathepsin D inhibition in the nanomolar range, high stability in synovial fluid and a long residence time in the joint capsule, for intraarticular administration in the treatment and/or prophylaxis of physiological and/or pathophysiological conditions, selected from the group consisting of arthrosis, traumatic cartilage injuries, arthritis, pain, allodynia and hyperalgesia, particularly preferably in the treatment and/or prophylaxis of arthrosis.

Pepstatin exhibits an advantageous biological activity which can easily be demonstrated in enzyme assays and animal experiments, as described in the examples. In such enzyme-based assays, pepstatin exhibits and causes an inhibiting effect, which is usually documented by $IC_{50}$ values in a suitable range, preferably in the micromolar range and particularly preferably in the nanomolar range.

Pepstatin can be administered to humans or animals, in particular mammals, such as apes, horses, dogs, cats, rats or mice, and can be used in the therapeutic treatment of the human or animal body and in the combating of the above-mentioned diseases. It can furthermore be used as diagnostic agent or as reagent.

Pepstatin can be used for the preparation of pharmaceutical preparations for intraarticular administration, in particular by non-chemical methods. In this case, it is brought into a suitable dosage form together with at least one solid, liquid and/or semi-liquid excipient and/or adjuvant and optionally in combination with one or more further active compound(s).

The invention therefore furthermore also relates, in particular, to pharmaceutical preparations for intraarticular administration comprising pepstatin and/or one of its physiologically acceptable salts, derivatives, solvates, prodrugs and stereoisomers, including mixtures thereof in all ratios, which comprise further excipients and/or adjuvants, and also to pharmaceutical preparations for intraarticular administration which comprise at least one further medicament active compound.

In particular, the invention also relates to a process for the preparation of a pharmaceutical preparation for intraarticular administration, characterised in that pepstatin and/or one of its physiologically acceptable salts, derivatives, solvates, prodrugs and stereoisomers, including mixtures thereof in all ratios, is brought into a suitable dosage form together with a solid, liquid or semi-liquid excipient and/or adjuvant and optionally with a further medicament active compound.

The pharmaceutical preparations according to the invention can be used as medicaments in human or veterinary medicine. The patient or host can belong to any mammal species, for example a primate species, particularly humans; rodents, including mice, rats and hamsters; rabbits; horses, cattle, dogs, cats, etc. Animal models are of interest for experimental investigations, where they provide a model for the treatment of a human disease.

Suitable carrier substances are organic or inorganic substances which are suitable for intraarticular administration and do not react with the compounds according to the invention. Owing to his expert knowledge, the person skilled in the art is familiar with which adjuvants are suitable for the desired medicament formulation. Besides solvents, for example water, physiological saline solution or alcohols, such as, for example, ethanol, propanol or glycerol, sugar solutions, such as glucose or mannitol solutions, or a mixture of the said solvents, and other active-compound carriers, it is also possible to use stabilisers and/or wetting agents, emulsifiers, salts for influencing the osmotic pressure, antioxidants, dispersants, antifoams, buffer substances, preservatives or solubilisers. If desired, preparations or medicaments according to the invention may comprise one or more further active compounds, for example one or more vitamins or active compounds which are effective in the prophylaxis and/or treatment of the above-mentioned medical indications.

If desired, preparations or medicaments according to the invention may comprise one or more further active compounds and/or one or more action enhancers (adjuvants).

The terms "pharmaceutical formulation" and "pharmaceutical preparation" are used as synonyms for the purposes of the present invention.

As used here, "pharmaceutically tolerated" relates to medicaments, precipitation reagents, excipients, adjuvants, stabilisers, solvents and other agents which facilitate the administration of the pharmaceutical preparations obtained therefrom to a mammal without undesired physiological side effects.

In the case of pharmaceutical preparations for parenteral administration, there is a requirement for isotonicity, euhydration and for tolerability and safety of the formulation (low toxicity), of the adjuvants employed and of the primary packaging. Surprisingly, pepstatin preferably has the advantage that direct use is possible and further purification steps for the removal of toxicologically unacceptable agents, such as, for example, high concentrations of organic solvents or other toxicologically unacceptable adjuvants, are unnecessary before use in pharmaceutical formulations.

The invention particularly preferably also relates to pharmaceutical preparations for intraarticular administration comprising pepstatin in precipitated non-crystalline, precipitated crystalline or in dissolved or suspended form, and optionally excipients and/or adjuvants and/or further pharmaceutical active compounds.

Pepstatin preferably enables the preparation of highly concentrated formulations without the occurrence of unfavourable undesired aggregations of pepstatin. Thus, ready-to-use solutions having a high active-compound content can be prepared with the aid of pepstatin with aqueous solvents or in aqueous media.

Pepstatin and/or physiologically acceptable salts and solvates thereof can also be lyophilised and the resultant lyophilisates used, for example, for the preparation of injection preparations for intraarticular administration.

Aqueous preparations for intraarticular administration can be prepared by dissolving or suspending pepstatin in an aqueous solution and optionally adding adjuvants. To this end, defined volumes of stock solutions comprising the said further adjuvants in defined concentration are advantageously added to a solution or suspension having a defined concentration of pepstatin, and the mixture is optionally diluted with water to the pre-calculated concentration. Alternatively, the adjuvants can be added in solid form. The amounts of stock solutions and/or water which are necessary in each case can subsequently be added to the aqueous solution or suspension obtained. Pepstatin can also advantageously be dissolved or suspended directly in a solution comprising all further adjuvants.

Pepstatin-containing solutions or suspensions having a pH of 4 to 10, preferably having a pH of 5 to 9, and an osmolality of 250 to 350 mOsmol/kg can advantageously be prepared. The pharmaceutical preparation can thus be directly administered intraarticularly substantially without pain. In addition, infusion solutions, such as, for example, glucose solution, isotonic saline solution or Ringer's solution, which may also comprise further active compounds, may also be added to the preparation for intraarticular administration, thus also enabling relatively large amounts of active compound to be administered.

Pepstatin is physiologically well tolerated, easy to prepare, can be dispensed precisely and is preferably stable with respect to assay, decomposition products and aggregates throughout storage and transport and during multiple freezing and thawing processes. It can preferably be stored in a stable manner over a period of at least three months to two years at refrigerator temperature (2-8° C.) and at room temperature (23-27° C.) and 60% relative atmospheric humidity (R.H.).

For example, pepstatin can be stored in a stable manner by drying and where necessary converted into a ready-to-use pharmaceutical preparation by dissolution or suspension. Possible drying methods are, for example, without being restricted to these examples, nitrogen-gas drying, vacuumoven drying, lyophilisation, washing with organic solvents and subsequent air drying, liquid-bed drying, fluidised-bed drying, spray drying, roller drying, layer drying; air drying at room temperature and further methods.

The term "effective amount" denotes the amount of a medicament or of a pharmaceutical active compound which causes in a tissue, system, animal or human a biological or medical response which is sought or desired, for example, by a researcher or physician.

In addition, the term "therapeutically effective amount" denotes an amount which, compared with a corresponding subject who has not received this amount, has the following consequence: improved treatment, healing, prevention or elimination of a disease, syndrome, condition, complaint, disorder or prevention of side effects or also a reduction in the progress of a disease, complaint or disorder. The term "therapeutically effective amount" also encompasses the amounts which are effective for increasing normal physiological function.

On use of preparations or medicaments according to the invention for intraarticular administration, pepstatin and/or physiologically acceptable salts and solvates thereof is generally used analogously to known, commercially available preparations. The dose here depends on the age, sex, weight and state of health and constitution of the patient, and the severity of his disease and other individual factors.

The pharmaceutical preparations according to the invention for intraarticular administration are preferably administered intraarticularly weekly to yearly, particularly preferably fortnightly to half-yearly, very particularly preferably monthly to quarterly.

The invention therefore furthermore relates to the use according to the invention of a pharmaceutical preparation according to the invention, where the pharmaceutical preparation according to the invention is administered intraarticularly as follows:
  a) weekly to yearly,
  b) fortnightly to half-yearly or
  c) monthly to quarterly.

The invention thus also relates to the use of pepstatin and/or one of its physiologically acceptable salts, derivatives, solvates, prodrugs and stereoisomers, including mixtures thereof in all ratios, for intraarticular administration in the treatment and/or prophylaxis of physiological and/or pathophysiological conditions, selected from the group consisting of arthrosis, traumatic cartilage injuries, arthritis, pain, allodynia and hyperalgesia, particularly preferably in the treatment and/or prophylaxis of arthrosis, where pepstatin and/or one of its physiologically acceptable salts, derivatives, solvates, prodrugs and stereoisomers, including mixtures thereof in all ratios, is administered intraarticularly as follows:
  a) weekly to yearly,
  b) fortnightly to half-yearly or
  c) monthly to quarterly.

However, the individual dose and administration intervals for a patient also depend on a large number of individual factors, such as, for example, on the efficacy of the particular compound used, on the age, body weight, general state of health, sex, nutrition, on the time and method of administration, on the excretion rate, on the combination with other medicaments and on the severity and duration of the particular disease.

A measure of the uptake of a medicament active compound in an organism is its bioavailability. If the medicament active compound is delivered to the organism intraarticularly in the form of an injection solution, its absolute bioavailability, i.e. the proportion of the pharmacon which reaches the joint gap in unchanged form, is 100%. Data on the pharmacokinetics, i.e. on the bioavailability, can be obtained analogously to the method of J. Shaffer et al. (J. Pharm. Sciences, 88 (1999), 313-318).

Furthermore, medicaments of this type can be prepared by means of one of the processes generally known in the pharmaceutical art.

Medicaments can be adapted for administration by the intraarticular route. Medicaments of this type can be prepared by means of all processes known in the pharmaceutical art by, for example, combining the active compound with the excipient(s) or adjuvant(s).

Intraarticular administration has the advantage that the compound according to the invention is administered directly into the synovial fluid in the vicinity of the joint cartilage and is also able to diffuse from there into the cartilage tissue. Pharmaceutical preparations according to the invention can thus also be injected directly into the joint gap and thus develop their action directly at the site of action as intended. The compound according to the invention is also suitable for the preparation of medicaments for intraarticular administration which have slow, sustained and/or controlled release of active compound. Pepstatin is thus also suitable for the preparation of delayed-release formulations, which are advantageous for the patient since administration is only necessary at relatively large time intervals.

The medicaments adapted to intraarticular administration include aqueous and non-aqueous sterile injection solutions comprising antioxidants, buffers, bacteriostatics and solutes, by means of which the formulation is rendered isotonic with the synovial fluid of the recipient to be treated; as well as aqueous and non-aqueous sterile suspensions, which can comprise suspension media and thickeners. The formulations can be delivered in single-dose or multi-dose containers, for example sealed ampoules and vials, and stored in the freeze-dried (lyophilised) state, so that only the addition of the sterile carrier liquid, for example water for injection purposes, immediately before use is necessary. Injection solutions and suspensions prepared in accordance with the formulation can be prepared from sterile powders, granules and tablets.

Pepstatin can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

Pepstatin can also be coupled to soluble polymers as targeted medicament excipients. Such polymers may include polyvinylpyrrolidone, pyran copolymer, polyhydroxypropylmethacrylamidophenol, polyhydroxyethylaspartamidophenol or polyethylene oxide polylysine, substituted by palmitoyl radicals. Furthermore, pepstatin can be coupled to a class of biodegradable polymers which are suitable for achieving slow release of a medicament, for example polylactic acid, poly-epsilon-caprolactone, polyhydroxybutyric acid, polyorthoesters, polyacetals, polydihydroxypyrans, polycyanoacrylates, polylactic-co-glycolic acid, polymers, such as conjugates between dextran and methacrylates, polyphosphoesters, various polysaccharides and polyamines and poly-ε-caprolactone, albumin, chitosan, collagen or modified gelatine and crosslinked or amphipatic block copolymers of hydrogels.

It goes without saying that, besides the constituents particularly mentioned above, the medicaments according to the invention may also comprise other agents usual in the art with respect to the particular type of pharmaceutical formulation.

Furthermore, the medicaments according to the invention can be used in order to provide additive or synergistic effects in certain known therapies and/or can be used in order to restore the efficacy of certain existing therapies.

Besides pepstatin, the pharmaceutical preparations according to the invention may also comprise further medicament active compounds, for example for use in the treatment of arthrosis, other cathepsin D inhibitors, NSAIDS, Cox-2 inhibitors, glucocorticoids, hyaluronic acid, azathioprine, methotrexate, anti-CAM antibodies, such as, for example, anti-ICAM-1 antibody and/or FGF-18. For the treatment of the other diseases mentioned, the pharmaceutical preparations according to the invention may, besides pepstatin, also comprise further medicament active compounds which are known to the person skilled in the art in the treatment thereof.

Even without further embodiments, it is assumed that a person skilled in the art will be able to utilise the above description in the broadest scope. The preferred embodiments should therefore merely be regarded as descriptive disclosure which is absolutely not limiting in any way.

The following examples are thus intended to explain the invention without limiting it. Unless indicated otherwise, percent data denote percent by weight. All temperatures are indicated in degrees Celsius. "Conventional work-up": water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate, filtered and evaporated, and the product is purified by chromatography on silica gel and/or by crystallisation.

Rf values on silica gel; mass spectrometry: EI (electron impact ionisation): $M^+$, FAB (fast atom bombardment): $(M+H)^+$, THF (tetrahydrofuran), NMP (N-methylpyrrolidone), DMSO (dimethyl sulfoxide), EA (ethyl acetate), MeOH (methanol), TLC (thin-layer chromatography)

Pepstatin has been synthesised and characterised. However, the preparation and characterisation of pepstatin can also be carried out by other methods for the person skilled in the art.

BRIEF DESCRIPTION OF THE DRAWINGS

FIG. 1 shows a table on stability data of pepstatin in synovial fluid,

FIG. 2 shows the pharmacokinetics-residence time data of pepstatin in the joint and in the plasma after intraarticular administration, FIG. 3 shows the pharmacokinetics-residence time data of pepstatin in the plasma after intravenous and oral administration, FIG. 4 shows an ACTL model for pepstatin efficacy in vivo in arthrosis.

EXAMPLE 1

Pepstatin—a Peptidic Cathepsin D Inhibitor

TABLE 1

Figure 5A:
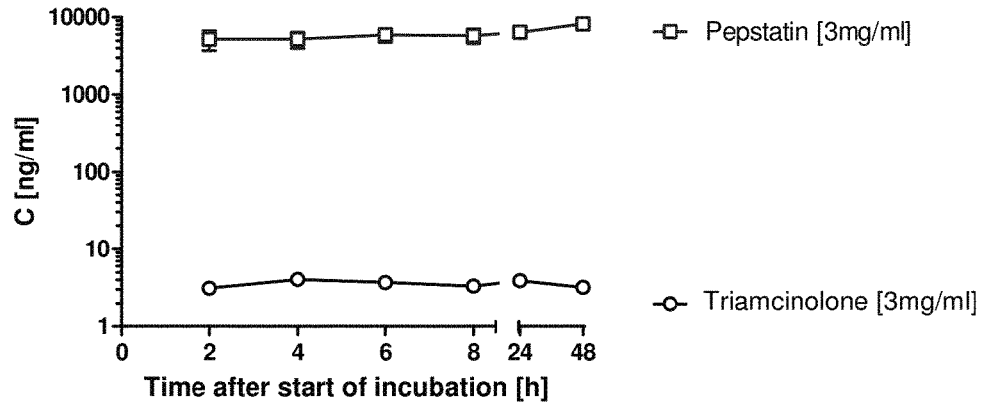
FIG. 5a shows in vitro microdialysis data for pepstatin in bovine synovial fluid.

| Structure | Cath D $IC_{50}$ [M] according to Example 2 | Cath D $IC_{50}$ [M] according to Example 3 |
|---|---|---|
| 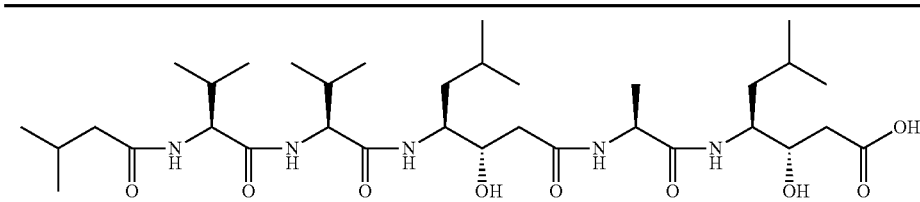 Pepstatin: (3S,4S)-3-hydroxy-4-[(S)-2-((3S,4S)-3-hydroxy-6-methyl-4-{(S)-3-methyl-2-[(S)-3-methyl-2-(3-methyl-butyrylamino)butyrylamino]butyrylamino}heptanoylamino)-propionylamino]-6-methylheptanoic acid | 1.6-1.90E−09 | 0.69-2.40E−09 | and physiologically acceptable salts, derivatives, solvates, prodrugs and stereoisomers thereof, including mixtures thereof in all ratios.

In addition, pepstatin is distinguished by high selectivity for cathepsin D over renin ($IC_{50}$>10,000 nM), good cartilage penetration and no measurable toxicity or genotoxicity.

EXAMPLE 2

In-Vitro Fluorescence Assay for Identification of Cathepsin D Inhibitors

In order to identify modulators of cathepsin D activity, a continuous enzymatic test was carried out with a synthetic peptide which carries a fluorescent group (MCA=(7-methoxycoumarin-4-yl)acetyl) which is quenched by energy transfer from a Dpn (2,4 dinitrophenyl) group on the same molecule, in Greiner 384-well nb microtitre plates. Cleavage of the peptidic substrate by cathepsin D causes an increase in the fluorescence intensity. In order to determine the efficacy of substances, the time-dependent increase in the fluorescence intensity in the presence of the substance was compared with the time-dependent increase in fluorescence in the absence of substances. The reference substance used was pepstatin A (Sigma-Aldrich). The substrate used was MCA-GKPILFFRLK(Dnp)d-R-NH$_2$ (Enzo Life Sciences, Lörrach). The enzyme employed was cathepsin D isolated from the human liver (Sigma-Aldrich) in a final concentration of 1.4 nM. The test was carried out in 100 mM sodium acetate buffer, 1.25% (v/v) of DMSO, 0.25% (w/v) of Chaps, pH 5.5. 2 µl of each substance solution with serially diluted substance concentration were added to in each case 4 µl of cathepsin D solution and incubated at room temperature for 10 min. The reaction was started by addition of 2 µl of substrate solution (final concentration 5 µM). After carrying out a starting-point fluorescence measurement (excitation wavelength 340 nm/emission wavelength 450 nm) using an Envision multilabel reader (Perkin Elmer), the reaction was incubated at room temperature for 60 min. The amount of peptide fragment cleaved off during the reaction time was subsequently measured by determination of the increase in the fluorescence intensity at 450 nm (excitation wavelength 340 nm).

Result: pepstatin inhibits cathpsin D in the nanomolar range (see Table 1).

EXAMPLE 3

Cartilage Explant Assay

In order to investigate the effect of potential cathepsin D inhibitors on cartilage degradation, a pH-induced model based on bovine explants is used. The pH of the medium in which the explants are cultivated is matched here to the pathophysiological pH of an arthrotic knee. This pH is pH 5.5. In this ex vivo model, potential cathepsin D inhibitors are subsequently investigated for their action with respect to arresting the cartilage degradation process. If the cartilage is destroyed, glycosaminoglycans (GAGs) are released into the cell culture supernatant. The amount of GAGs released can be determined quantitatively with the aid of DMMB (dimethylmethylene blue hydrochloride). If sulfated GAGs are detected using dimethylmethylene blue hydrochloride, the decrease in the absorption at 633 nm is utilised. Since it is also possible to use very low GAG concentrations, a dye/GAG complex does not precipitate out even after extended incubation of DMMB with GAG, which sometimes happens after only a short time in other measurement methods. In order to determine the concentration, a calibration line is also recorded using chondroitin sulfate. The GAG values can be used to calculate an IC$_{50}$ value, i.e. a concentration at which a substance exhibits 50% of its action.

Solutions:
Incubation Medium, pH 7.4:
DMEM without FBS, addition of 1% of Pen/Strep and 30 µg/ml of ascorbic acid, the medium is not stored.
Incubation Medium, pH 5.5:
DMEM without FBS, the pH is adjusted by addition of MES and monitored using a pH meter, addition of 1% of Pen/Strep and 30 µg/ml of ascorbic acid.
Solutions for the GAG Measurement:
DMMB Colouring Solution (V=500 ml):
Dissolve 8 mg of DMMB (dimethylmethylene blue) in 2.5 ml of ethanol+1 g of sodium formate+1 ml of formic acid, make up to 500 ml with bidistilled water.
Incubation Medium:
FBS (medium without FBS)
Chondroitin Sulfate Solutions (Standard Curve)
Preparation of standard solutions with the following concentrations: 50 µg/ml; 25 µg/ml; 12.5 µg/ml; 6.25 µg/ml; 3.125 µg/ml; 1.5 6 µg/ml; 0.78 µg/ml and a blank control of the medium. The preparation of the standard solution is carried out in the medium with which the experiment was also carried out.

1.) Procedure: pH-Induced Cartilage Degradation of Bovine Explants

The bovine explants are firstly prepared. The induction of the cartilage degradation is carried out in 96-multiwell plates. One explant is cultivated per well. In each case, 200 µl of DMEM (incubation medium pH 5.5) without FBS+30 µg/ml of ascorbic acid are added. As negative control, explants (n=4) are incubated at pH 7.4 (without FBS). This control is not included in the calculation of the data, but instead ensures that the pH change has the desired effect on the release of GAG. At this point, the substances to be tested are added. No pre-incubation of the explants is carried out. The explants are cultivated with the corresponding substances for 3 days in the incubator at 37° C. and 7.5% CO$_2$.

2.) Incubation Procedure

In order to investigate the effect of cathepsin D inhibitors on the liberation of GAG (glycosaminoglycan), the substances are employed in the desired concentration and cultivated for 3 days. The compounds to be tested are tested in a first experiment in a concentration of 1 µM and 1% of DMSO. Substances which have an effect of >50% on the liberation of GAG (this corresponds to <50% of the control in the Assay Explorer) are tested in the next experiment at 100 nM and 1% of DMSO. Substances which have an effect of >50% on the release of GAG under these conditions (this corresponds to <50% of the control in the Assay Explorer) are tested in a concentration/action relationship. The compounds here are investigated in the following concentrations: 30 µM, 10 µM, 3 µM, 1 µM, 0.3 µM, 0.1 µM, 0.03 µM, 0.01 µM.

The positive control used is pepstatin A with a concentration of 0.01 µM. The assay window is defined by the control (pH 5.5), defined as 0% effect, and the control pH 5.5+0.01 µM pepstatin A, defined as 100% effect. After incubation for 3 days, the cell culture supernatants are collected and stored at −20° C. or measured directly. The amount of GAG released is measured photometrically.

The effect (1 value) of the respective substance in % based on the positive control (pH 5.5+0.01 µM pepstatin A) and the negative control (pH 5.5) is reported for concentrations of 1 µM and 100 nM. The value represents the average of 4 replicates. In the determination of a concentration/action relationship, an IC$_{50}$ value is reported to the database (Assay Explorer).

4.) Measurement

The cell culture supernatants (200 µl) are either measured directly or stored at −20° C. To ensure an accurate determination of the concentration (µg/ml of GAG in the supernatant) of GAG, the measurement values must be located in the linear region of the standard curve. In order to ensure this, various dilutions are routinely introduced (⅕, 1/10, 1/20, 1/40). The dilutions are prepared with medium and introduced automatically (Hamilton) into a 384-multiwell plate (15 µl). 60 µl of DMMB solution are likewise added automatically (or using a multichannel pipette). A rapid colour reaction occurs, which is subsequently measured at 633 nm using a plate reader (for example Envision).

Depending on the amount of sample present, at least one double determination is carried out.

The data are provided by the MTP reader as csv or xls files and stored as raw data based on this format (xls) or used for the calculation of the percentage effect of the particular compound.

5.) Quality Controls

As control for the induction of the pH-induced cartilage degradation, 4 explants are incubated at pH 7.4. This corresponds to the physiological pH of the cartilage, and no effect on the release of GAG is thus expected here. These GAG values (μg/ml of supernatant) are thus always significantly lower than the GAG values for incubation at pH 5.5.

A further control, which both serves for checking of the experiment, but is also important for the definition of the assay window, is the pepstatin control (pH 5.5+0.01 μM pepstatin A). This substance non-specifically blocks the activity of most proteases and thus determines the maximum possible effect of a compound.

6.) Results

Pepstatin exhibits an $IC_{50}$ value in the nanomolar range in the GAG assay (see Table 1).

(1) Klompmakers, A. & Hendriks, T. (1986) Anal. Biochem. 153, 80-84, Spectrophotometric Detection of Sulfated Glycosaminoglycans.

(2) Groves, P. J. et al. (1997) Anal. Biochem. 245, 247-248 Polyvinyl alcohol-stabilised binding of sulfated GAGs to dimethylmethylene blue.

EXAMPLE 4

Investigation of the Anti-Hyperalgesic Action in Animals

In order to induce an inflammation reaction, a carrageenan solution (CAR, 1%, 50 μl) was injected intraarticularly on one side into a rat knee joint. The uninjected side was used for control purposes. Six animals per group were used. The threshold was determined by means of a micrometer screw (medial-lateral on the knee joint), and the thermal hyperalgesia was determined by means of a directed infrared light source by the Hargreaves method (Hargreaves et al. 1988) on the sole of the foot. Since the site of inflammation (knee joint) is different from the site of measurement (sole of the paw), use is made here of the term secondary thermal hyperalgesia, the mechanisms of which is of importance for the discovery of effective analgesics.

Experimental description of thermal hyperalgesia (Hargreaves test): the experimental animal is placed in a plastic chamber on a quartz sheet. Before testing, the experimental animal is firstly given about 5-15 minutes time to familiarise itself with the environment. As soon as the experimental animal no longer moves so frequently after the familiarisation phase (end of the exploration phase), the infrared light source, whose focus is in the plane of the glass bottom, is positioned directly beneath the rear paw to be stimulated. An experiment run is then started by pressing the button: infrared light results in an increase in the skin temperature of the rear paw. The experiment is terminated either by the experimental animal raising the rear paw (as an expression of the pain threshold having been reached) or by automatic switching-off of the infrared light source when a pre-specified maximum temperature has been reached. Light reflected by the paw is recorded as long as the experimental animal sits still. Withdrawal of the paw interrupts this reflection, after which the infrared light source is switched off and the time from switching on to switching off is recorded. The instrument is calibrated in such a way that the infrared light source increases the skin temperature to about 45 degrees Celsius in 10 s (Hargreaves et al. 1988). An instrument produced by Ugo Basile for this purpose is used for the testing.

CAR was purchased from Sigma-Aldrich. Administration of the specific cathepsin D inhibitors according to the invention was carried out intraarticularly 30 minutes before the CAR. Triamcinolone (TAC) 10 μg/joint was used as positive control, and the solvent (vehicle) was used as negative control. The hyperalgesia is quoted as the difference in the withdrawal times between the inflamed and the non-inflamed paw.

Result: TAC was capable of reducing the CAR-induced swelling, but pepstatin was not. In contrast, pepstatin was able to reduce the extent of thermal hyperalgesia as a function of the dose.

Assessment: it has been shown that pepstatin exerts an anti-hyperalgesic action. This can be postulated since pepstatin exhibits no influence on inflammatory swelling and thus on the hyperalgesia trigger. It can thus be assumed that pepstatin develops a pain-reducing action in humans.

EXAMPLE 5

Stability of Pepstatin in Bovine Synovial Fluid

1.) Extraction of Bovine Synovial Fluid

In the preparation of bovine explants (for the diffusion chamber or other assays), either cow hoof (metacarpal joints) or cow knee are used. The synovial fluid can be obtained from both joints. To this end, the synovial fluid is carefully removed from the open joint using a 10 ml syringe and a cannula and transferred into prepared 2 ml Eppendorf vessels. The Eppendorf vessels are labelled depending on the animal (cow passport is available). It must be ensured here that blood does not enter the joint gap during preparation of the joints. If this is the case, the synovial fluid becomes a reddish colour and must consequently be discarded. The synovial fluid is basically highly viscous and clear to yellowish in colour. The removal together with a macroscopic analysis of the synovial fluid is documented.

2.) Batch for Stability Testing of Substances in SF

In order to check the stability of individual compounds, a pool of 4 different bovine synovial fluids is mixed. To this end, about 1 ml per SF are used. The mixture is prepared directly in a 5 ml glass vessel in order to minimise any absorption effects. The SFs are mixed thoroughly, but carefully. No air bubbles or foam should form. To this end, a vortex unit is used at the lowest speed. The compounds to be tested are tested in an initial concentration (unless requested otherwise) of 1 μM. After addition of the substance, the batch is again mixed thoroughly and carefully. For visual monitoring, all SF batches are photographed, and the pictures are filed in the eLabBio file for the corresponding experiment. The batches are incubated in the incubator for 48 h at 37° C. and 7.5% $CO_2$.

3.) Sampling

The sampling is carried out after the pre-agreed times (unless requested otherwise, see below). 4×200 μl of the SF are removed from the mixture at each point in time and transferred directly into 0.5 ml "low-binding" Eppendorf vessels. "Low-binding" Eppendorf vessels are used in order to minimise interaction of the substances with the plastic of the vessels. In each case 200 μl of acetonitrile have already been introduced into the Eppendorf vessel, so that a 1+1 mixture of the SF forms thereafter. This simplifies the subsequent analysis, but precipitation of the protein may occur immediately after addition of the SF. This should be noted on the record. The 0 h sample is taken immediately after addition of the substance. This corresponds to the 100% value in the stability calculation. Ideally, the concentration employed should be retrieved here. The samples can be frozen at −20° C.

0 h
6 h
24 h
48 h

The negative control used is SF without substance. The positive control used is SF with 1 μM of substance. This corresponds to the 0 h value and thus 100% stability.

The samples are stored in "low-binding" Eppendorf vessels at −20° C. The samples are subsequently measured quantitatively. The detection of the corresponding substances is carried out by mass spectrometry.

4.) Data Processing

The concentrations measured (ng/ml) are plotted against time in a graph (Graph Pad Prism®). The percentage stability of the substance is determined here. The 100% value used is the initial value in SF at time 0 h. The data are stored in eLabBio under the respective experiment number and reported in the MSR database (as percent stability after the corresponding incubation times).

5.) Results

Pepstatin remains stable over a period of at least two weeks in synovial fluid (see FIG. 1).

EXAMPLE 6

Pharmacokinetic Data after Intraarticular Injection

For this study (KK-Rat-12-003), 14 male Lister hooded rats were used. All rats were given a single intraarticular injection into both knee joints at time "0". An injection consisted of 30 μl in which about 700 μg of compound were homogeneously suspended (suspension=compound in 0.5% Methocel K4M with 0.25% Tween20 in PBS). The suspension was administered via a 25 G cannula. No peculiarities were noted with respect to any changes of in-life parameters, such as, for example, body weight, knee swelling or relieving postures. At each point in time indicated in Table 2, animals were sacrificed, the knee joints were prepared (removal of skin and muscle tissue) and frozen for further processing.

The deep-frozen joints were briefly thawed, comminuted as well as possible using bone scissors, and 4 times the volume of 80% ethanol was subsequently added. The mixture was subsequently homogenised using an Ultraturrax, the extract was shaken at RT for 20 min and then stored at −20° C. for at least 30 min. The mixture was then centrifuged at 13,000 rpm for 5 min, a 10 μl aliquot of the supernatant was diluted 1:5000 with internal standard solution, transferred into a PCR plate and analysed.

20 μl of internal standard solution were added to 20 μl of plasma, 100 μl of methanol were added, and the mixture was shaken for 5 min. The extracts were then stored at −20° C. for at least 30 min and subsequently centrifuged at 13,000 rpm for 5 min. 80 μl of the supernatant were transferred into a PCR plate and analysed.

All samples were analysed with the aid of a UPLC-MS/MS system. The detection limits for pepstatin were 0.1 ng/ml in plasma and 8 μg/g in tissue.

TABLE 2

| | Knee joint diameter in mm | | |
|---|---|---|---|
| Days after injection | Average joint diameter [mm] | SD | N (injected joints) |
| 0 | 10.08 | 0.31746745 | 28 |
| 1 | 10.88 | 0.49042038 | 26 |
| 2 | 10.50 | 0.30862869 | 16 |
| 4 | 10.12 | 0.19734488 | 16 |
| 7 | 10.35 | 0.19478086 | 16 |
| 9 | 10.14 | 0.18101258 | 10 |
| 11 | 10.37 | 0.15579188 | 10 |
| 13 | 10.24 | 0.17707444 | 8 |
| 15 | 10.45 | 0.15238579 | 8 |
| 20 | 10.18 | 0.15942605 | 6 |
| 27 | 10.50 | 0.11189281 | 6 |

After intraarticular administration of a suspension, pepstatin exhibits an average residence time of about 106 h in the knee joint in the rat and only very low systemic exposure owing to slow release from the synovium and very high clearance in the blood. Pepstatin exhibits so-called flip-flop kinetics in the plasma, i.e. the terminal plasma half life is not determined by the elimination, but instead by the release of pepstatin from the suspension and diffusion via the synovial membrane. However, pepstatin was detectable in the plasma at a very low concentration up to 28 days after administration (see FIG. 2).

EXAMPLE 7

Pharmacokinetic Data after Intravenous (i.v.) and Oral (p.o.) Administration

The pharmacokinetic parameters of pepstatin were determined in Wistar rats (BW about 250 g), after administration of the test substance in a cocktail of up to 4 substances. Pepstatin was administered to the male rats (n=3 per type of administration) either by means of an i.v. bolus injection into the tail vein or via oral gavage by means of a stainless-steel cannula. The test substances were dissolved in DMSO/PEG200/water (2/60/38 v/v) with a final concentration of 0.8 mg/ml, and a dose of 0.2 mg/kg i.v. and 0.5 mg/kg orally was administered. Blood samples (200 μl) were taken via the sublingual vein with light isoflurane anaesthesia at the following times after administration: iv: 0.1, 0.5, 1, 2, 4, 6 and 24 h; po: 0.25, 0.5, 1, 2, 4, 6 and 24 h.

The blood samples were collected in centrifuge tubes containing Li heparin and centrifuged at about 10,000 g at 4° C. for 3 min. The plasma obtained therefrom was immediately frozen at −20° C. and stored until analysis. The plasma concentrations were determined by means of a standard LC-MS/MS method. The pharmacokinetic parameters (Clp, Vss, T1/2, F) were determined via an NCA analysis.

After intravenous administration, pepstatin exhibits very high clearance (>100% liver blood flow), an average distribution volume and consequently a very short plasma half life (about 0.14 h). After oral administration, all plasma concentrations were below the detection limit (see FIG. 3).

EXAMPLE 8

Efficacy (In Vivo) of Pepstatin in Arthrosis—ACLT tMx Model

Rats were selected as experimental animals. After shaving and disinfection, the operation area is opened by means of a medial skin cut with a length of about 1 cm. The knee joint capsule is prepared and the medial patellar ligament is exposed. After opening of the joint capsule, cutting of the medial parapatellar ligaments and lateral displacement of the patella, the anterior cruciate ligament is cut using a curved knife with a blunt end (ACLT=anterior cruciate ligament transection). The anterior and posterior ligaments holding the meniscus in place are subsequently prepared and cut and the meniscus is removed tMx (resection of the medial meniscus). After repositioning of the patella, the joint is finally rinsed with sterile saline solution in order to remove any blood coagulum that may have formed.

The patella is repositioned, and the medial patellar ligament is re-fixed by means of continuous suture with sealing of the capsule. The muscles are likewise sutured. The skin is subsequently closed by means of single stitches. The operation duration is about 10 minutes. The postoperative trial duration was 6 weeks.

For intraarticular injection, the animals are anaesthetised with 1.5-2% by vol. of isoflurane. Before the injection, buprenorphine is injected subcutaneously. The injection area is gently shaved and disinfected. The knee joint is brought into a slightly bent position, and the substance to be tested or the vehicle is injected into the joint.

For the present experiment, 1 mg of pepstatin in 30 µl was employed. As negative control, only vehicle was injected into one trial group. As positive control, the non-operated hind leg of the rat was used in each case.

Processing in Histology

The tissue samples taken are fixed in paraformaledhyde (4%) for at least 72 hours and then rinsed under flowing tap water for 24 hours. The samples are subsequently decalcified by means of Osteosoft over a period of 4 weeks. The tissue was then infiltrated with paraffin and histological sections having a thickness of 7 µm were prepared. For assessment, the sections were stained with Safranin O Fast Green.

Assessment

Two sections in the region of the exposure zone were selected from each animal and assessed by two experienced people using an assessment system. The assessment system is based on the work by V. B. Kraus et al (Osteoarthritis & Cartilage, 18, S3, 2010).

Results

Pepstatin also exhibits significant efficacy in vivo in arthrosis (see FIG. 4)

EXAMPLE 9

Microdialysis

The free medicament levels at the site of action are crucial for the action of a medicament. In the case of intraarticular injections, the distribution space in the synovial fluid is of great interest in this respect.

Since the synovial fluid on the one hand represents a complex matrix for the analytical determination of peptides and on the other hand only the free, i.e. non-protein-bound medicament fraction is relevant for the action, the microdialysis method was employed. The eluate obtained from the microdialysis enables analysis of free medicament levels from the complex matrix of the synovial fluid. The reason for this is that a barrier membrane (microdialysis membrane) which only molecules up to a certain size is able to pass through is employed. This "pore size" determines the concentration of the medicament in the eluate besides the flow rate of the eluate and the free concentration of medicament present in the synovial fluid as driving force for material exchange.

For these investigations, microdialysis probes from CMA (reference number 000082; CMA 7; microdialysis sample 1 mm 3/pkg) fitted with a cuprophane membrane and having a pore size of 6 kDa were used. The eluate flow rate was 0.5 µl/min.

Firstly, release kinetics in bovine synovial fluid were investigated and compared with triamcinolone (Triam Injekt® 20 mg)—a medicament approved for intraarticular injection. Triamcinolone was employed here in the predissolved crystal suspension whereas the pepstatin crystals were added directly to the synovial fluid without dissolution. 3 mg of medicament per ml of synovial fluid were employed in a glass vessel, which corresponds approximately to the concentration conditions after intraarticular injection into the knee joint. Amazingly, and in contrast to triamcinolone, very high levels of unbound pepstatin were measured. The more or less constant levels also suggest a fast dissolution rate with high stability of pepstatin in synovial fluid (see FIG. 5a)

Figure 5B:
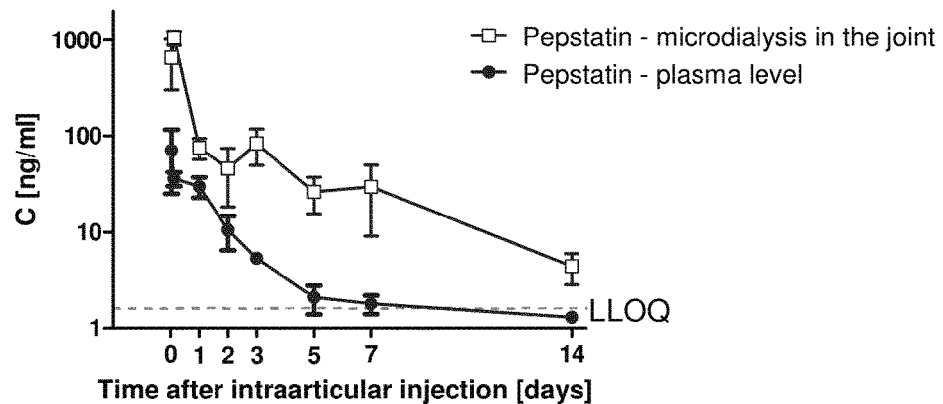
FIG. 5b shows in vivo microdialysis data for pepstatin in guinea pig knee joint.
Figure 5C:
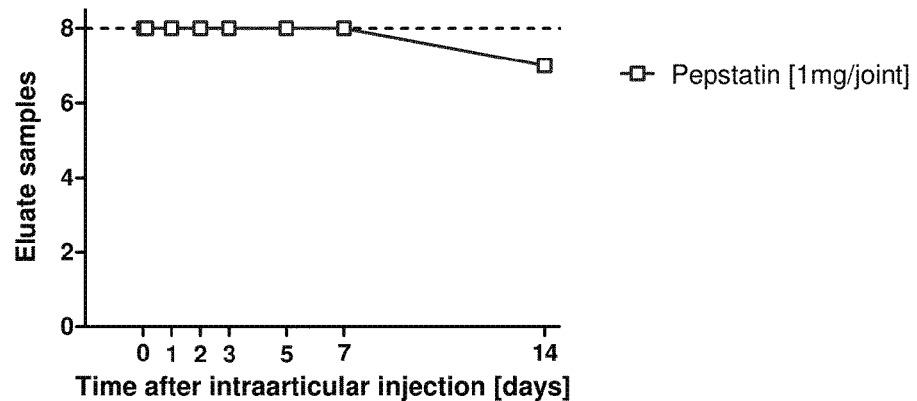
FIG. 5c shows positive pepstatin presence in eluate samples.

Owing to the high solubility of pepstatin in synovial fluid, the results from joint microdialysis on guinea pigs (Dunkin Hartley) are surprising: up to 14 days after intraarticular injection of pepstatin [1 mg/joint administered in 50 µl as suspension], significant levels of pepstatin are detectable in the joint and that in virtually all eluates investigated (see FIGS. 5b and 5c).

The invention claimed is:

1. A method for the treatment and/or prophylaxis of physiological and/or pathophysiological conditions, selected from the group consisting of arthrosis, traumatic cartilage injuries, arthritis, pain, allodynia and hyperalgesia, comprising intraarticular administration to a patient in need of said treatment of a pharmaceutical preparation
   comprising pepstatin and/or one of its physiologically acceptable salts, solvates, prodrugs and stereoisomers, including mixtures thereof in all ratios, and one or more excipients and/or adjuvants, said preparation formulated for intraarticular administration for the treatment and/or prophylaxis of said physiological and/or pathophysiological conditions,
   wherein the pharmaceutical preparation is formulated for administration weekly to yearly, and
   wherein the pharmaceutical preparation is administered weekly to yearly.

2. The method of claim 1, for the treatment and/or prophylaxis of arthrosis.

3. A method for the treatment and/or prophylaxis of physiological and/or pathophysiological conditions, selected from the group consisting of arthrosis, traumatic cartilage injuries, arthritis, pain, allodynia and hyperalgesia, comprising intraarticularly administering to a patient in need thereof pepstatin and/or one of its physiologically acceptable salts, solvates, prodrugs and stereoisomers, including mixtures thereof in all ratios,
   wherein the pepstatin and/or one of its physiologically acceptable salts, solvates, prodrugs and stereoisomers is administered weekly to yearly.

4. A method for the treatment and/or prophylaxis of arthrosis, comprising intraarticularly administering to a patient in need thereof pepstatin and/or one of its physiologically acceptable salts, solvates, prodrugs and stereoisomers, including mixtures thereof in all ratios, wherein the pepstatin and/or one of its physiologically acceptable salts, solvates, prodrugs and stereoisomers, including mixtures thereof in all ratios, is administered weekly to yearly.

5. The method of claim 1, wherein the preparation is administered fortnightly to half-yearly.

6. The method of claim 1, wherein the preparation is administered monthly to quarterly.

7. The method of claim 2, wherein the preparation is administered fortnightly to half-yearly.

8. The method of claim 2, wherein the preparation is administered monthly to quarterly.

9. The method of claim 3, wherein the pepstatin and/or one of its physiologically acceptable salts, solvates, prodrugs and stereoisomers, including mixtures thereof in all ratios, is administered fortnightly to half-yearly.

10. The method of claim 3, wherein the pepstatin and/or one of its physiologically acceptable salts, solvates, prodrugs and stereoisomers, including mixtures thereof in all ratios, is administered monthly to quarterly.

11. The method of claim 4, wherein the pepstatin and/or one of its physiologically acceptable salts, solvates, prodrugs and stereoisomers, including mixtures thereof in all ratios, is administered fortnightly to half-yearly.

12. The method of claim 4, wherein the pepstatin and/or one of its physiologically acceptable salts, solvates, prodrugs and stereoisomers, including mixtures thereof in all ratios, is administered monthly to quarterly.

* * * * *